United States Patent [19]
Ozaki

[11] Patent Number: 5,995,581
[45] Date of Patent: Nov. 30, 1999

[54] CR IMAGE-BASED POSITIONING FOR X-RAY CT SCAN

[75] Inventor: Masahiro Ozaki, Otawara, Japan

[73] Assignee: Kabushiki Kaisha Toshiba, Kawasaki, Japan

[21] Appl. No.: 08/802,432

[22] Filed: Feb. 18, 1997

[30] Foreign Application Priority Data

Feb. 15, 1996 [JP] Japan .................................. 8-028023

[51] Int. Cl.$^6$ .................................................. G01N 23/00
[52] U.S. Cl. .................................................. 378/20; 378/4
[58] Field of Search .................................................. 378/20, 4

[56] References Cited

U.S. PATENT DOCUMENTS

| | | | |
|---|---|---|---|
| 4,649,555 | 3/1987 | Matsubayashi | 378/20 |
| 4,730,351 | 3/1988 | Heumann | 378/20 |
| 5,327,474 | 7/1994 | Inoue et al. | 378/20 |
| 5,661,772 | 8/1997 | Bar et al. | 378/20 |

FOREIGN PATENT DOCUMENTS

6-90949  4/1994  Japan .

*Primary Examiner*—Craig E. Church
*Attorney, Agent, or Firm*—Oblon, Spivak, McClelland, Maier & Neustadt, P.C.

[57] ABSTRACT

In X-ray CT scan, slice positions to be scanned by an X-ray CT scanner can be determined readily and accurately by substituting a CR image for a conventionally used scanogram. An X-ray diagnostic system comprises an X-ray fluoroscopy apparatus providing a CR(computed radiography) image composed of digital pixel values produced from X-rays transmitted through an object subjected to fluoroscopic X-rays. The system also comprises an X-ray CT scanner, coupled with x-ray fluoroscopy apparatus, providing a tomographic image of the object. The system further comprises an element for obtaining positional information required for tomographic imaging of the object using the CR image and an element for enabling the X-ray fluoroscopy apparatus and the X-ray CT scanner to use in common the positional information. As a result, for example, a slice position of the object, as the positional information, required for the X-ray CT scanner is obtained and provided for the X-ray CT scanner.

9 Claims, 8 Drawing Sheets

CR IMAGE-BASED POSITIONING FOR X-RAY CT SCAN

BACKGROUND OF THE INVENTION

1. Field of the Invention

The present invention relates to a compound diagnostic X-ray system made by combining an X-ray fluoroscopy apparatus with an X-ray CT scanner. More particularly, this invention is concerned with a diagnostic X-ray system enabling use of information of slice positions in common between the X-ray CT fluoroscopy apparatus and the X-ray CT scanner in a manner that the slice positions are determined using a computed-radiography (CR) image produced from the X-ray fluoroscopy apparatus.

2. Description of the Related Art

In general, for producing tomographic images of a diagnostic region of a patient body using an X-ray CT scanner, it is necessary to determine slice positions accurately. For determining slice positions, the X-ray CT scanner produces an X-ray fluoroscopic image referred to as a scanogram. The slice positions are determined by a physician or the like (operator) while the scanogram is being viewed.

Figure 1A:
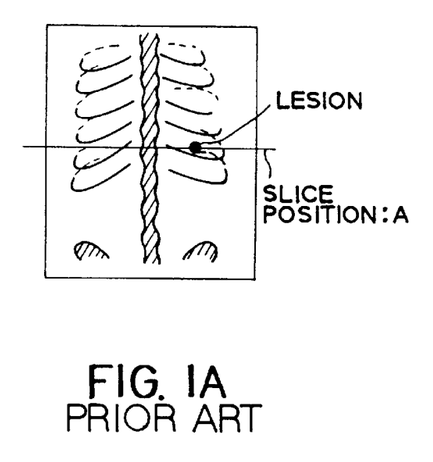
FIGS. 1A and 1B are diagrams showing models of a prior art scanogram with a slice position determined and a tomographic image of the slice position respectively.
Figure 1B:
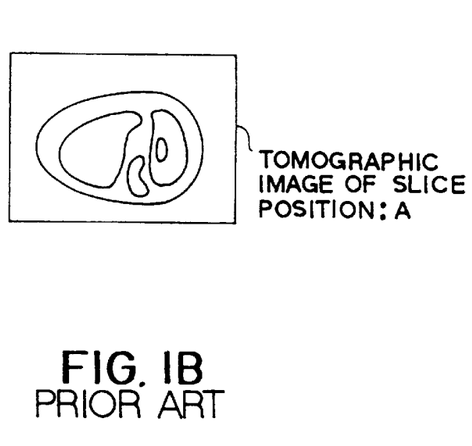

For example, in the case of a rotate-rotate CT scanner, an X-ray tube and detectors are not rotated but held stationary, and X-rays are irradiated while a patient (couch) is being moved unidirectionally (for example, one direction along a body-axis direction of a patient) at a comparatively slower constant speed. In this case, as shown in FIG. 1A, a scanogram analogous to an ordinary X-ray fluoroscopic image is produced. A physician or the like determines slice positions (in FIG. 1A, for example, slice position A of a slice containing a lesion). In the X-ray CT scanner, an X-ray scan is performed at the determined slice positions, thus tomographic images are provided, as shown in FIG. 1B, for example.

However, the scanogram is, as mentioned above, produced by irradiating X-rays while the patient couch is being moved for a certain interval. A scan time gets longer by the time required for moving the patient couch. In other words, the scanogram is not an instantaneously-produced image unlike an X-ray fluoroscopic image. There is therefore difficulty in accurately imaging a region that makes a quick motion (for example, a vessel). It is sometimes hard to determine slice positions accurately.

Moreover, needed as a patient X-ray dose is at least an exposure dose obtained by irradiating X-rays for the period of time required for moving the patient couch. From the viewpoint of minimizing an X-ray dose, desirably, an X-ray fluoroscopic image of a patient should be produced with instantaneous exposure alone.

In almost all cases, the scanogram produced by an X-ray CT scanner is inferior to a fluoroscopic image (CR image), which is a digitized image produced by an X-ray TV unit or the like including, for example, a two-dimensional detector such as an image intensifier (I.I.) and a TV camera, in terms of contrast and resolution. It is therefore hard to locate a lesion using the scanogram. This results in an increase in time required for determining slice positions, and brings about not only the fear of lacking precision in determining slice positions but also remarkably increased time for the scan planning which will lower the patient throughput.

SUMMARY OF THE INVENTION

The present invention attempts to break through the foregoing situation. An object of the present invention is to enable ready and accurate determination of slice positions to be scanned by an X-ray CT scanner while minimizing an exposure dose and ensuring an efficient maneuverability.

Another object of the invention is to use information of slice positions in a multiplicity of modes, such as used for the tomographic imaging with an X-ray CT scanner and used as indices in retrieving a desired one among a plurality of tomographic CT-images for interpretation of CT-images.

According to an aspect of the present invention for accomplishing the objects, there is provided an X-ray diagnostic system comprising: an X-ray fluoroscopy apparatus providing a CR(computed radiography) image composed of digital pixel values produced from X-rays transmitted through an object subjected to fluoroscopic X-rays; an X-ray CT scanner, coupled with x-ray fluoroscopy apparatus, providing a tomographic image of the object; means for obtaining positional information required for tomographic imaging of the object using the CR image; and means for enabling the X-ray fluoroscopy apparatus and the X-ray CT scanner to use in common the positional information.

Preferably, the obtaining means consists of means for obtaining a slice position of the object, as the positional information, required for the X-ray CT scanner and said enabling means consists of means for providing the X-ray CT scanner the slice position.

In this case, it is preferred that the X-ray fluoroscopy apparatus comprises an X-ray source radiating the X-rays, an imaging unit detecting the transmitted X-rays, a convertor converting outputs of the imaging unit into digital values of image data, and a monitor visualizing the image data as the CR image.

It is also preferred that the obtaining means comprises an input device enabling an operator to manually specify a desired position in the CR image visualized by the monitor, and means for setting the slice position corresponding to the specified desired position through the input device. For example, the setting means is composed of means setting the slice position based on first positional information representing an absolute position of a frame of the CR image within the object and second positional information inherently given to pixels of the CR image. In one embodiment, the setting means includes means for correcting the set slice position into another slice position being in accord with a height of a rotation center set in a gantry of the X-ray CT scanner.

It is still preferred that the setting means is composed of means setting the slice position based on first positional information representing an absolute position of a frame of the CR image within the object, second positional information inherently given to pixels of the CR image, and third positional information of a rotation center of a gantry of the X-ray CT scanner.

Preferred is that the X-ray diagnostic system further comprises a couch, on which the subject is laid for diagnosis, used in common by both the X-ray fluoroscopy apparatus and the X-ray CT scanner.

Still preferred with regard to the X-ray diagnostic system, the X-ray fluoroscopy apparatus is an X-ray TV system for cardiovascular examination constituting an interventional radiology (IVR)-CT/angiography system in conjunction with the X-ray CT scanner.

Also preferably, the X-ray CT scanner comprises a storage member storing a plurality of the tomographic images indexed image by image by the slice position and said enabling means includes means for retrieving among the plurality of the tomographic image stored in the storage member a tomographic image corresponding to the slice position and means for displaying the retrieved tomographic image.

As a second aspect of the present invention, there is provided a method of positioning an imaging position in an X-ray diagnostic system comprising an X-ray fluoroscopy apparatus and an X-ray CT scanner both of which are combined for an integrated form of the X-ray diagnostic system, the method comprising the steps of: using the X-ray fluoroscopy apparatus, producing a CR (computed radiography) image composed of digital pixel values produced from X-rays transmitted through an object subjected to fluoroscopic X-rays; determining desired positional information required for tomographic imaging of the object using the CR image; and providing the positional information to the X-ray CT scanner.

As a third aspect of the present invention, there is provided an X-ray CT scanner for providing a tomographic image of an object sliced at a slice position set to the object, comprising: means for receiving information concerning the slice position given externally, said slice position being obtained using a CR (computed radiography) image composed of digital pixel values produced from X-rays transmitted through the object subject to fluoroscopic X-rays; and means for performing an X-ray tomographic scan at the received slice position of the object.

According to the present invention, desired slice positions (slice positions of which images a physician or the like wants to see) coincident with an object region are set using a CR image, which is produced through digitization by an X-ray fluoroscopy apparatus, representing an area to be imaged containing the object region of a patient body. Tomographic images of the set slice positions can then be produced and displayed (or some of tomographic images stored in advance can be read out and displayed).

In other words, since determining slice positions to be scanned by an X-ray CT scanner can be achieved using a higher spatial resolution CR image produced by instantaneous X-ray exposure, slice positions can be determined shortly and accurately with a reduced exposure dose. Consequently, precision in diagnosis of an object region can be improved.

DESCRIPTION OF THE PREFERRED EMBODIMENTS

Referring to the appended drawings, a first embodiment of the present invention will be described below.

Figure 2:
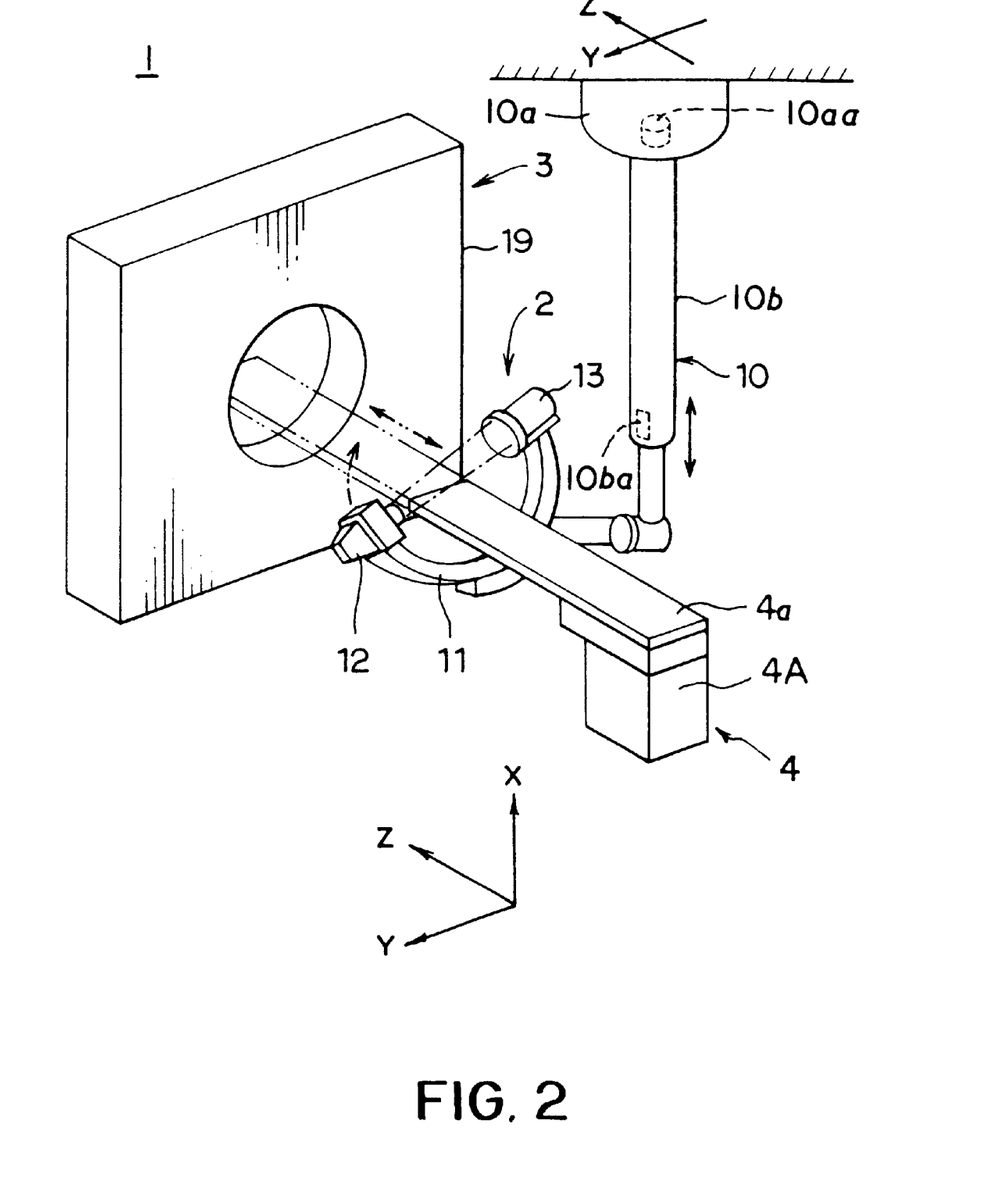
FIG. 2 is a diagram schematically showing the overall configuration of a diagnostic X-ray system in accordance with the first embodiment of the present invention.
Figure 3:
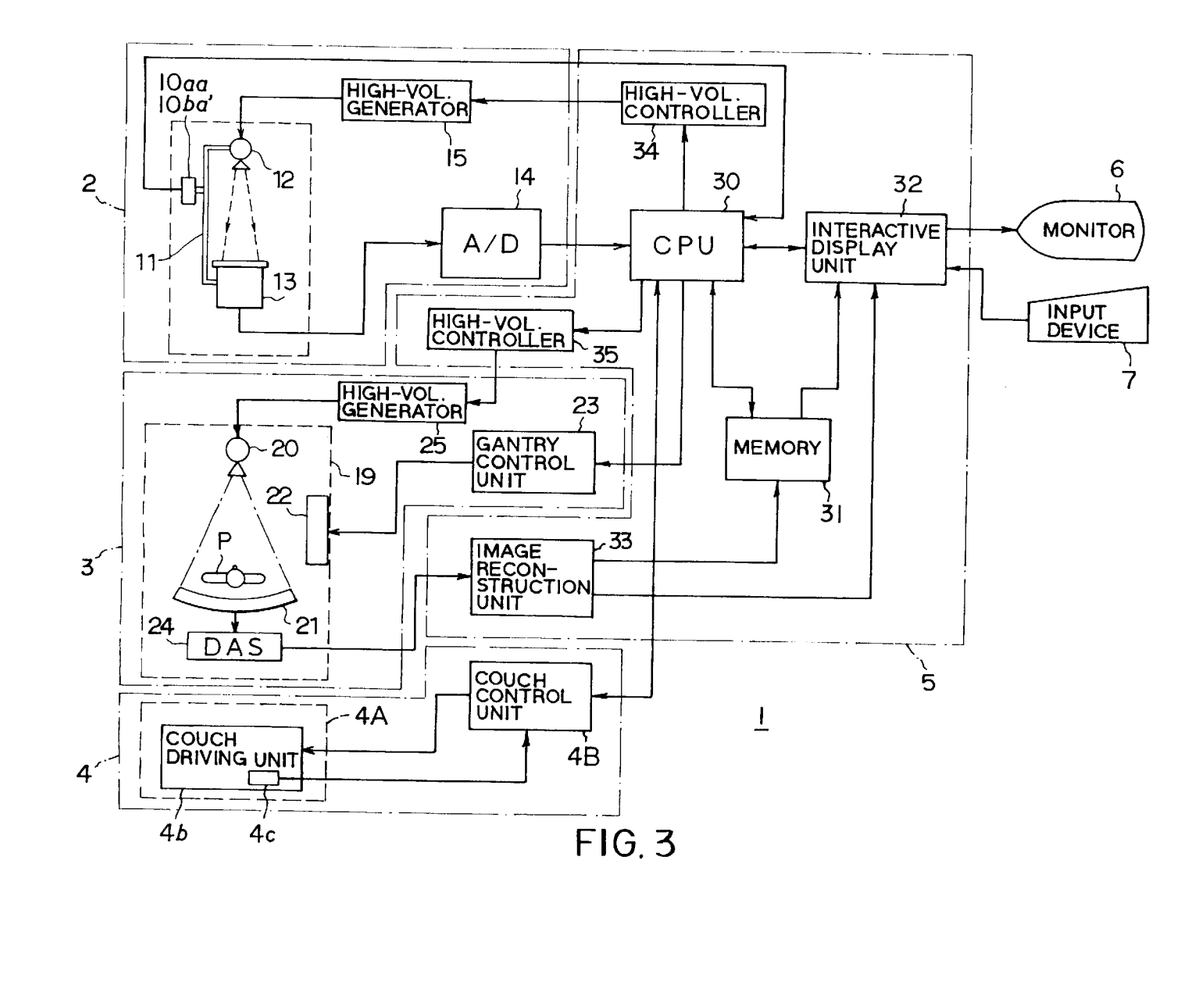
FIG. 3 is a block diagram schematically showing the system configuration of circuitry of the diagnostic X-ray system in accordance with the first embodiment of the present invention.

FIG. 2 is a diagram schematically showing a diagnostic X-ray system of the present invention comprising functionally an X-ray CT scanner (refers to only its gantry portion) and X-ray fluoroscopy apparatus (refers to only its radiating body portion). FIG. 3 is a block diagram schematically showing the electrical circuitry of the diagnostic X-ray system.

A diagnostic X-ray system 1 shown in FIGS. 2 and 3 comprises an X-ray fluoroscopy apparatus 2 and an X-ray CT scanner 3, in addition to a patient couch portion 4, console 5, monitor 6, and input device 7 that are components to be shared by the fluoroscopy apparatus 2 and CT scanner 3. The patient couch portion 4 has a patient couch 4A and a couch control unit 4B.

A couchtop 4a is placed on the top of the patient couch 4A while being supported so that the couchtop 4a can slide in its longitudinal Z-direction (normally, corresponds to the body-axis direction of a patient). A patient P can lie down on the couchtop 4a. Around the patient couch 4A, there are placed the X-ray fluoroscopy apparatus 2 and X-ray CT scanner 3, apart from each other by an appropriately-set distance within the range of a stroke of the couchtop 4a, with the patient couch 4A used in common. Sliding the couchtop 4a provides the diagnostic X-ray system 1 having multi-functions, where a patient P can be freely transported from the zone of the X-ray fluoroscopy apparatus 2 to the zone of the X-ray CT scanner 3, and vice versa. In the couch driving unit 4b, a slide sensor 4c is arranged to detect a current sliding position of the couchtop 4a on the basis of the driven state of the couch driving unit 4b. The detected signal by the sensor 4c is then sent to the couch control unit 4B.

The couch control unit 4B has circuitry controlling the operation of the couch driving unit 4b in conformity with a command from a CPU in the console 5, which will be described later. The circuitry can also include another CPU as its main component. The couch control unit 4B controls the couch driving unit 4b on the basis of a sliding position (target value) sent from the CPU of the console 5 and a detected sliding position indicative of a current sliding position (actual value). Additionally, the patient couch 4A is also adjustable concerning its height.

The X-ray fluoroscopy apparatus 2 includes a movable curved arm 11 such as a C-shaped arm or omega-shaped arm suspended on the ceiling by a support 10 (the description will proceed on the assumption that the C-shaped arm (C-arm) is employed). An X-ray tube 12 and an I.I.-TV system (imaging unit) 13 composed of an I.I. and high spatial resolution TV camera are installed on opposite sides of the C-arm 11 with the patient couch 4 positioned between them. This arrangement permits the X-ray tube 12 and the imaging unit 13 to be faced with each other.

In the X-ray fluoroscopy apparatus 2, the support 10 is capable of traveling the entire C-arm 11 at least three-dimensionally in the X-, Y- and Z-directions. (In the orthogonal coordinate, the Z-direction corresponds to the longitudinal direction of the couchtop 4a.) The support 10 includes a ceiling-attaching portion 10a enabling two-dimensional travel in the Y-Z plane parallel to the ceiling and a pillar portion 10b enabling one-dimension travel along the X(height)-direction. In the ceiling-attaching portion 10a, a traveling detection sensor 10aa is disposed to detect a two-dimensional traveling position of the support 10. In the pillar portion 10b, another traveling detection sensor 10ba is disposed to detect a traveling position of the support 10 along the height direction. The traveling detection sensors 10aa and 10ba are composed by including an encoder or potentiometer, outputting digital signals indicative of traveling positions to the CPU of the console 5.

Fluoroscopy is carried out by irradiating X-rays from the X-ray tube 12 to the patient P on the couchtop 4a that has slid to a given imaging position in the X-ray fluoroscopy apparatus 2. X-rays transmitted by the patient P during the irradiation are detected as an analog fluoroscopic image by the I.I. and TV camera of the imaging unit 13. The analog fluoroscopic image is converted into digital CR image data of higher spatial resolution having a given number of pixels and a given pixel size by an A/D converter 14 connected to the imaging unit 13, and then sent to the CPU of the console 5. The X-ray tube 1 2 is coupled with a high-voltage generator 15, which is then coupled with a high-voltage controller of the console 5. Although the A/D converter 14 is one component of the X-ray fluoroscopy apparatus 2 side in the embodiment, the converter 14 may be incorporated within the console 5 to be described later.

Figure 4:
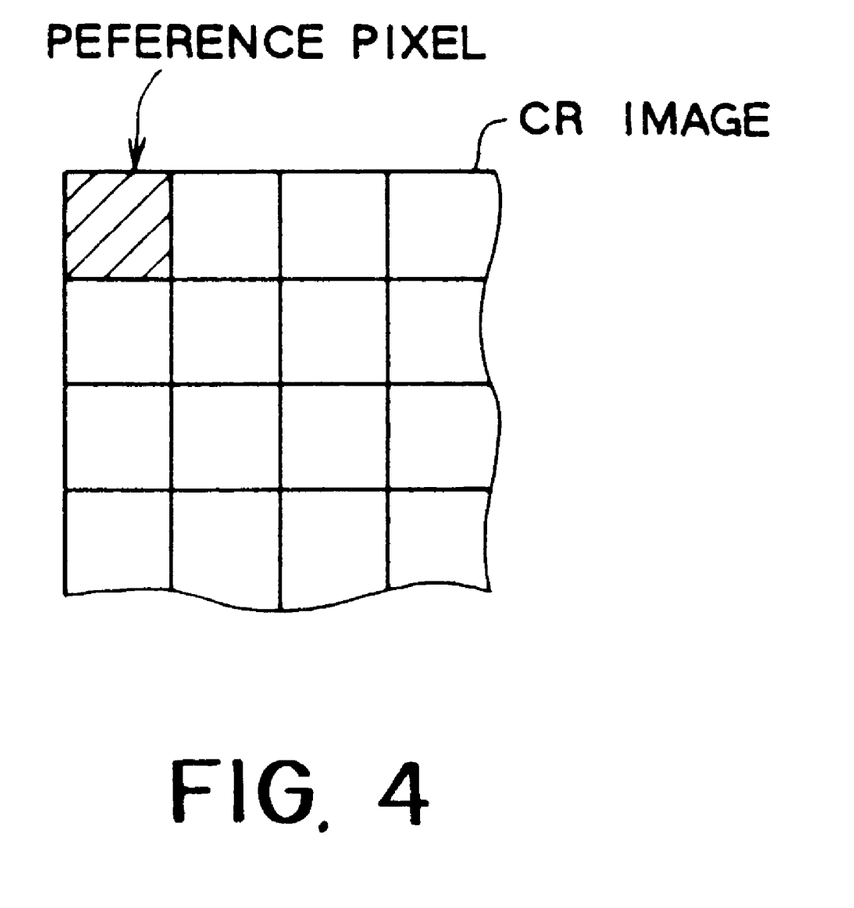
FIG. 4 is a diagram conceptually showing a reference pixel in a CR image.

Image data sent to the CPU of the console 5 is, as mentioned above, digital image data whose pixel size is predetermined. As the pixel size is predetermined, a position in the digital image can be designated or identified by specifying a distance from a pixel serving as a reference. In other words, CR image data inherently self-contains information of specifying positions in the CR image data. For example, assuming that a pixel size (matrix size) is M×M, as shown in FIG. 4, if the leftmost pixel is indicated as (1, 1) and used as a reference, every position in the CR image data can be expressed with the number of pixels starting with the reference pixel (1, 1) in a row or column direction (or the number of pixels×a pixel size=a distance). Thus knowing an absolute position of the CR frame image measured from a reference position of an object permits each unknown position (consists of one or more pixels) on the CR image to be specified absolutely to the object (to the reference position of the object).

On one hand, the X-ray CT scanner 3 is constructed to be driven according to, for example, a rotate-rotate (R-R) method. Specifically, the scanner 3 includes a gantry 19 within which an X-ray tube 20 and X-ray detector 21 are placed face to face through an approximate cylindrical opening for diagnosis. The couchtop 4a (patient P lying down on the couchtop) will be slid into the opening to realize a given position within the gantry 19.

A scan is performed by the scanner 3 as described below. That is to say, a given slice position of the patient P is aligned with a slit-like scan position of the gantry 19, and an X-ray beam emanating from the X-ray tube 20 is irradiated to the patient P. In this state, the X-ray tube 20 and X-ray detectors 21 are rotated, for example, 360° in unison by means of a gantry moving mechanism 22. The rotation drive is controlled by a gantry control unit 23 which receives a command from the console 5. The unit 23 has a CPU, for example, for such control. The X-ray tube 20 is coupled with a high-voltage generator 25 coupled with a later-described high-voltage controller of the console 5.

During the rotation, the X-ray detector 21 detect X-rays (X-ray intensify distribution) transmitted by a certain slice position of the patient P as X-ray data (current data proportional to X-ray intensities) at intervals of a certain angle. X-ray data detected by the X-ray detector 21 is subjected to pre-processing such as A/D conversion and signal amplification by a data acquisition system (DAS) 24, and acquired as projection data for each slice. The projection data acquired by the data acquisition system 24 is sent to an image reconstruction unit of the console 5.

The console 5 comprises, as shown in FIG. 3, a CPU 30 responsible for the entire control of the system, a memory 31 and an interactive display unit 32 both coupled with the CPU 30, and an image reconstruction unit 33. The console 5 also comprises high-voltage controllers 34 and 35 assigned for the fluoroscopy apparatus side and scanner side, respectively.

Among those, the CPU 30 has connection with the A/D converter 14 and sensors 10aa and 10ba, and also with the interactive display unit 32, memory 31, and high-voltage controllers 34 and 35. The CPU 30 is further connected with the gantry control unit 23 and couch control unit 4B. The CPU 30, as an example, is to perform the processing shown in FIG. 5. To be specific, the CPU 30 reads not only image data of a CR image from the X-ray fluoroscopy apparatus 2 but also detected signals from the sensors 10aa and 10ba for necessary processing. The CPU 30 communicates with the interactive display unit 32 for necessary display information. Still the CPU 30 controls both the couch control unit 4B and gantry control unit 23, and receives the detection signal, indicative of a current slide position of the couchtop 4a, via the couch control unit 4B from the slide sensor 4c. Still the CPU 30 stores and reads image data to and from the memory 31.

The image reconstruction unit 33 reads projection data acquired by the DAS 24 and carries out computation of, for example, convolution back projection of the projection data, whereby a reconstructed tomographic CT image is produced for each slice position. The image reconstruction unit 33 is coupled with the interactive display unit 32 and the memory 31 storing image data of tomographic image data reconstructed. Alternatively, the image reconstruction unit 33 may be incorporated in the side of the X-ray CT scanner 3 instead of being in the side of the console 5.

The interactive display unit 32 is coupled with the monitor 6 and input device 7, and act as an interface between the monitor (display system) and input device (input system) and the CPU (other processing system). The interactive display unit 32 also includes another CPU to convert numerical data or position data entered at the input unit 7 into data that can be handled by the CPU 30, and then sends the resultant data to the CPU 30, or sets the order of displaying reconstructed images sent from the image reconstruction unit 33 or memory 31.

The monitor 6 is used to display an X-ray fluoroscopic image and reconstructed tomographic CT images. The input device 7 is constructed by including a keyboard or mouse permitting a physician or the like (operator) to input various kinds of information to the whole system 1.

Next, the operations of the whole diagnostic X-ray system having the foregoing components will be described with reference to FIG. 5.

Figure 5:
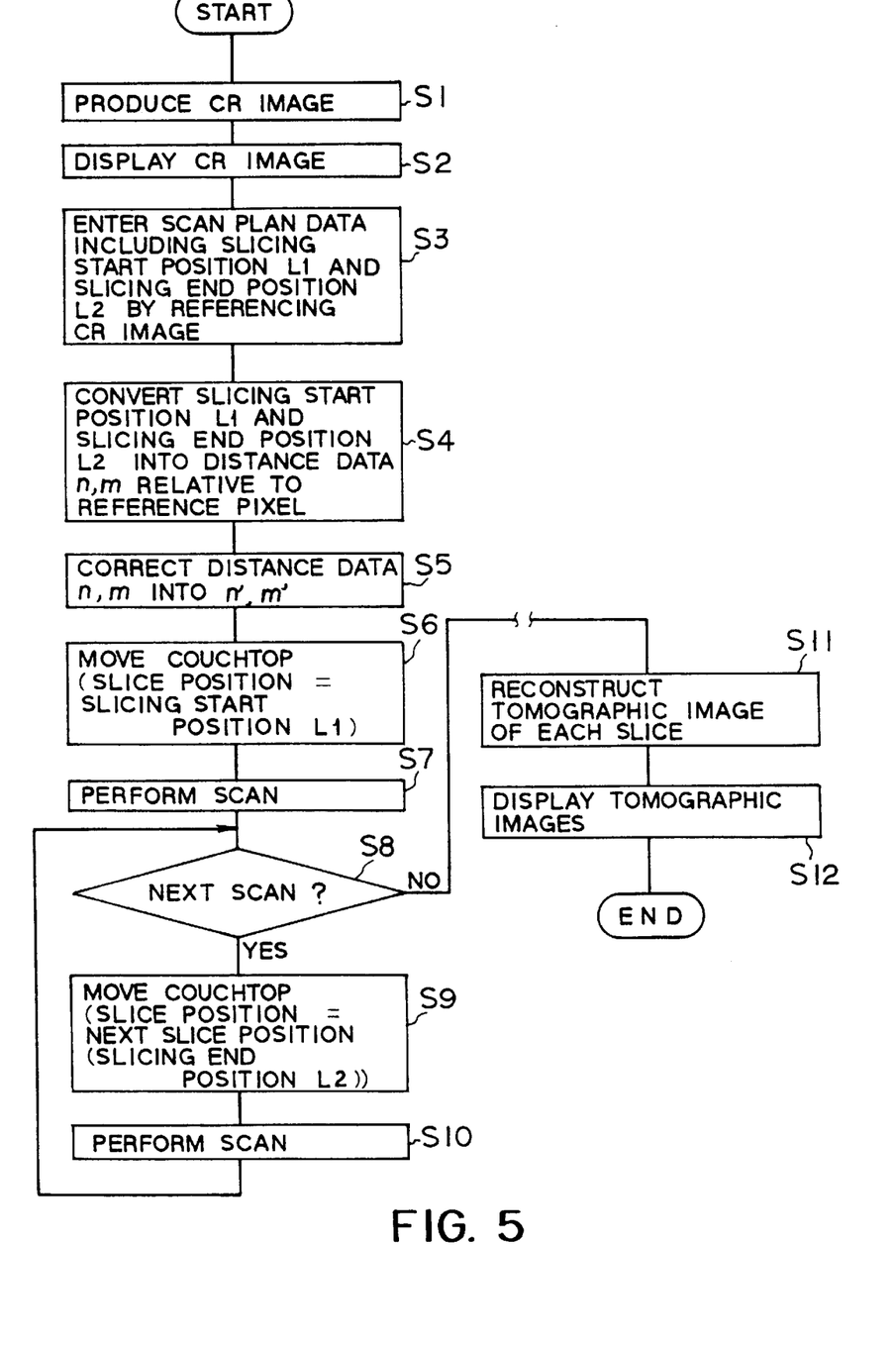
FIG. 5 is a brief flowchart describing an example of processing performed by the whole diagnostic X-ray system for the purpose of making a CT scan plan and carrying out the planned scan.

First, the scan planning required for scan of the X-ray CT system 3 is carried out through steps S1 to S4 of FIG. 5.

At step S1, the CPU 30 sends a command of fluoroscopy for a CR image in the X-ray fluoroscopy apparatus 2. To be specific, to determine slice positions, a scan pitch, or the like, the command of fluoroscopy of a CR image representing a lesion of the patient P is sent to the high-voltage controller 34 and couch control unit 4B. In response to the command, the couch control unit 4B controls driving of the couch driving unit 4b according to position information detected by the slide sensor 4c, whereby the patient P (couchtop 4a) is positioned at a given scan position (a position at which the lesion is at least included in a fluoroscopy range) for X-ray fluoroscopy by the X-ray fluoroscopy apparatus 2. At this positioning, the high-voltage controller 34 send to the high-voltage generator 15 a command for irradiating X-rays and makes the X-ray fluoroscopy unit 2 execute aforesaid fluoroscopy. CR image data representing the lesion, which results from the fluoroscopy, is sent through the A/D converter 14 to the CPU 30.

Concurrently at step S1, an absolute Z-directional position it self of the fluoroscopic CR image to a preset reference position of the patient is determined on the signals detected by the slide sensor 4c and/or traveling detection sensors 10aa and 10ba.

At step S2, the CPU 30 display a CR image on the monitor 6 using the CR image data obtained by the fluoroscopy. Specifically, the CPU 30 stores the sent CR image data in an internal memory or the memory 31, performs given digital image processing on the CR image data, sends resultant CR image data to the monitor 6 via the interactive display unit 32. As a result, a CR image representing the lesion of the patient P, which has higher spatial resolution than a conventional scanogram acquired by the X-ray CT scanner, is displayed on the monitor 6 as shown in FIG. 6, for example.

At step S3, the CPU 30 instructs the interactive display unit 32 to acquire data of a scan plan. A physician identifies the size and location of the lesion while viewing the CR image displayed on the monitor 6, and makes a scan plan. Specifically, the physician manipulates the keyboard or mouse of the input device 7 while referencing the CR image, and enters a scan pitch, the number of slices, slice position information (slicing start and end positions are included), and the like. Scan plan data including slice position information, a scan pitch, and the like designated (entered) using the input device 7 is sent to the CPU 30 via the interactive display unit 32.

Figure 6:
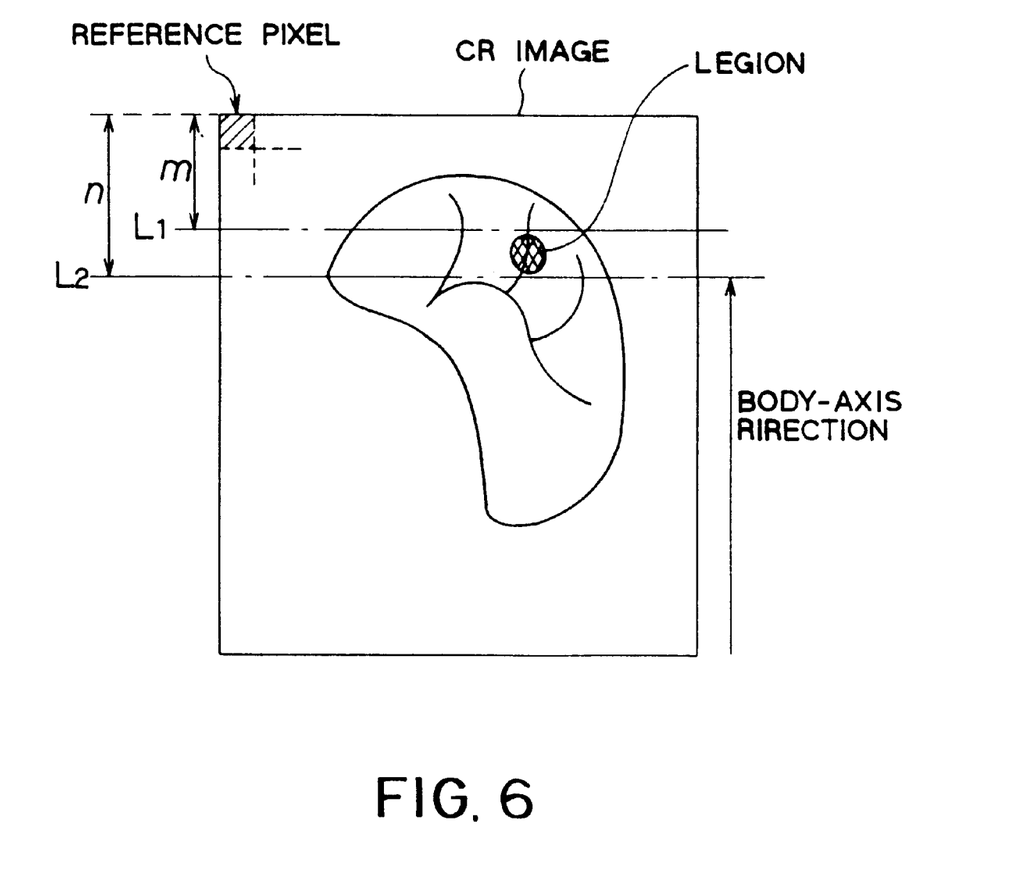
FIG. 6 is a diagram showing a model of a CR image in which slicing start and end positions, and distances of the slicing start and end positions from a reference pixel are specified.

For example, a physician enters, as shown in FIG. 6, slice line L1 (slicing start position) and slice line L2 (slicing end position) orthogonal to the body-axis direction as slice position information in a CR image by manipulating the mouse or the like of the input device 7.

Then at step S4, the CPU 30 converts the specified slice positions in the CR image into their actual position data. Specifically, the CPU 30 reads and memorizes the sent scan plan data including slice position information, a scan pitch, and the like. Finally, the CPU 30 converts the slice position information included in the scan plan data into data of the number of pixels starting with a reference pixel (or distance data (the number of pixels×a pixel size)) by referencing the CR image data stored in the internal memory. In this embodiment, the slicing start position L1 shall be converted into distance data m (mm) indicating a distance m from the reference pixel, and the slicing end position L2 shall be converted into distance data n (mm) indicating a distance n from the reference pixel. In this conversion, additional processing is done such that absolute position data of the CR image is added to the converted distance data n, m, the absolute position data being indicative of an absolute distance from the preset reference of the object in the Z-direction and being stored after being detected when the fluoroscopy had been made (refer to step S1). This addition enables the distance data m and n to be given absolute slicing start position m and slicing end position n to the object.

At step S5, the CPU 30 corrects the converted distance data m, n to be slightly adjusted.

Figure 7:
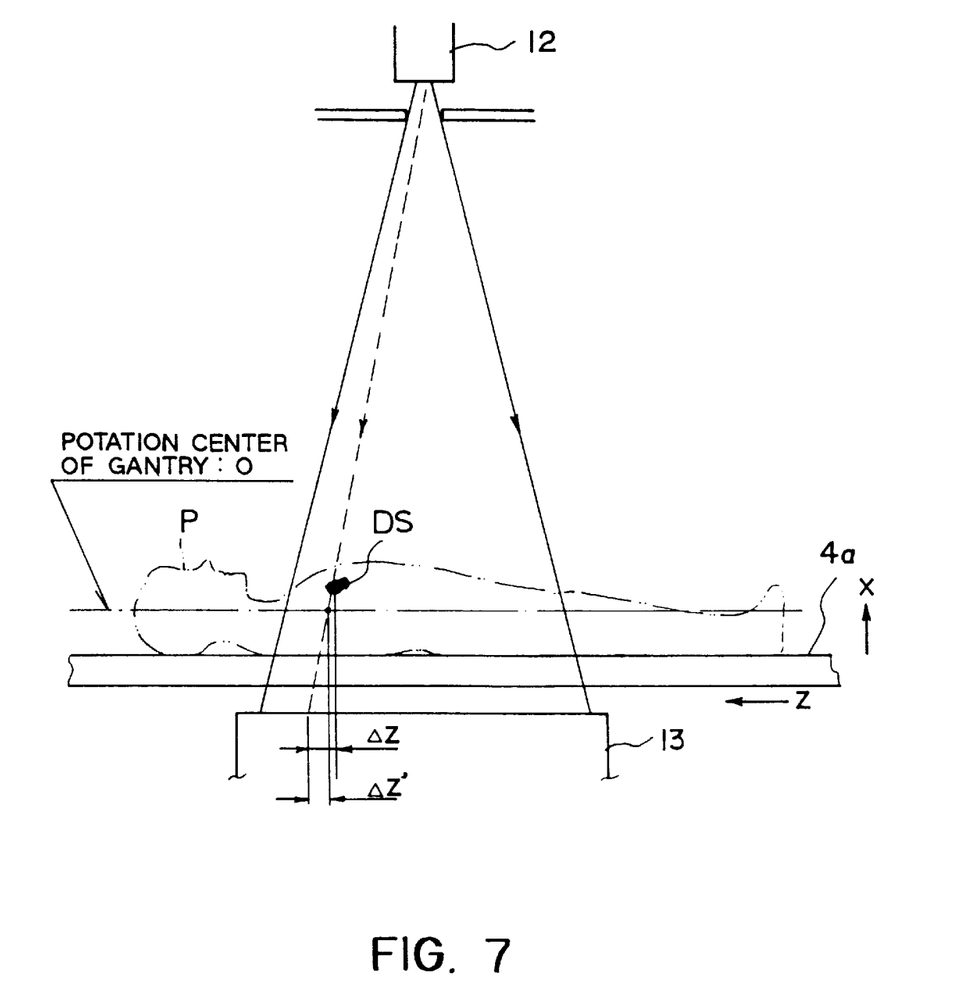
FIG. 7 shows a difference in slice positions depending on different X-directional heights.

This correction is performed under the following reason. Control of slice positions using as-converted distance data m, n in an X-ray CT scanner is equivalent to the fact that slice positions are changed in the height level the same as incidence surface of X-rays of I.I. However, owing to the fact that actual X-ray beams irradiating from the X-ray tube is spread over the slicing Z-direction in a cone-like shape, as shown in FIG. 7, there is a slight difference between the actual slice positions of an object and the slice positions designated on the CR image at positions other than the center axis of the X-ray beam in the slicing Z-direction. FIG. 7 exemplifies this situation where there occurs a positional slice difference $\Delta z$ with regard to a lesion DS.

Although respective lesions have different heights (positions in the X-direction), their heights may be regarded as being approximately equal to the height of the rotation center of the gantry of the X-ray CT scanner. In the case of the FIG. 7, the difference $\Delta z$ concerning the lesion DS may be considered to be approximate equal a difference $\Delta z'$ associated with the height of the rotation center O of the gantry.

Thus, in this embodiment, as a compromised and practical height position, the height of the rotation center O of the gantry is employed. And the distance data m, n are converted into a new set of distance data m', n' corresponding to slice positions in the height of the rotation center O. This correction conversion is performed based on pre-stored geometry data including the height of the patient couch (couchtop), the height of the rotation center of the gantry, the heights of the X-ray tube and I.I. in the X-direction, respectively.

Then, at steps S6 to S10, the CPU 30 actuates the X-ray CT scanner 3 according to the scan plan data and carries out a CT scan.

To be more specific, first, the CPU 30 sends a couchtop move command to the couch control unit 4B. The couch control unit 4B controls driving of the couch driving unit 4b while referencing the calculated and corrected distance data m' and the current position data of the couchtop 4a detected in real time by the slide sensor 4c, and slides the couchtop 4a so that the scan position of the gantry 19 coincides with the entered slicing start position L1 in the CR image (step S6).

Thereafter, the CPU 30 allows the gantry control unit 23 to control driving of the gantry 19 according to the entered scan plan data such as a specified scan pitch, and carries out the scan at slicing start position L1 (step S7).

The CPU 30 then determines whether or not there remains one or more slices to be scanned by making reference to the planned total slice number (step S8). When the determination is that there remains one or more slices to be scanned, the CPU 30 again send the couchtop move command to another couch control unit 4B. This allows the couch control unit 4B to control driving of the couch driving unit 4b while referencing the current position data of the couchtop 4a detected by the slide sensor 4c, and slides the couchtop 4a by a scan pitch (step S9). The scan for a new slice is then carried out under the control of the CPU 30 (step S10).

The foregoing processing of steps S8 to S10 is repeated until a scan is carried out at slicing end position L2 on the basis of the input and corrected distance data n'.

As a result, projection data of slices existent between slicing start position L1 and slicing end position L2 is acquired by the DAS 24. Therefore, when the CPU 30 notifies the image reconstruction unit 33 of scan end, it reconstructs each tomographic image of the slices (step S11). The reconstructed tomographic images are displayed successively on the monitor 6 via the interactive display unit 32 (step S12).

As mentioned above, according to this embodiment, the location and size of a lesion are grasped properly while a CR image having remarkably higher spatial resolution than a conventional scanogram produced by an X-ray CT scanner is being viewed. Scan plan data such as slice positions and a scan pitch can be set according to the location and size of the lesion. Based on the set scan plan data automatically and on-line provided to the X-ray CT scanner, the CT scanner carries out a scan. In other words, scan plan data including slice positions is set using a high-spatial resolution CR image produced by the X-ray fluoroscopy apparatus. Slice positions (a slicing start position and slicing end position) can be set on the basis of the set data. As a result, the slice positions can be determined accurately and shortly. In addition, increased are maneuverability associated with positioning of slices and patient throughputs.

As described previously, a CR image is produced instantaneously by the X-ray fluoroscopy apparatus. Unlike production of a conventional scanogram produced by an X-ray CT scanner, it is unnecessary to slide the couch (couchtop). A region making a quick motion such as blood can be visualized accurately, which not only contributes to higher accuracy of setting slice positions and shorter operation time for setting slice positions but also minimizes an exposure dose compared with the conventional scanogram produced by an X-ray CT scanner.

This embodiment has been described on the assumption that a CR image is used to plan a scan. The present invention is not limited to this usage but can apply to a usage of a second embodiment described below (See FIG. 8).

Figure 8:
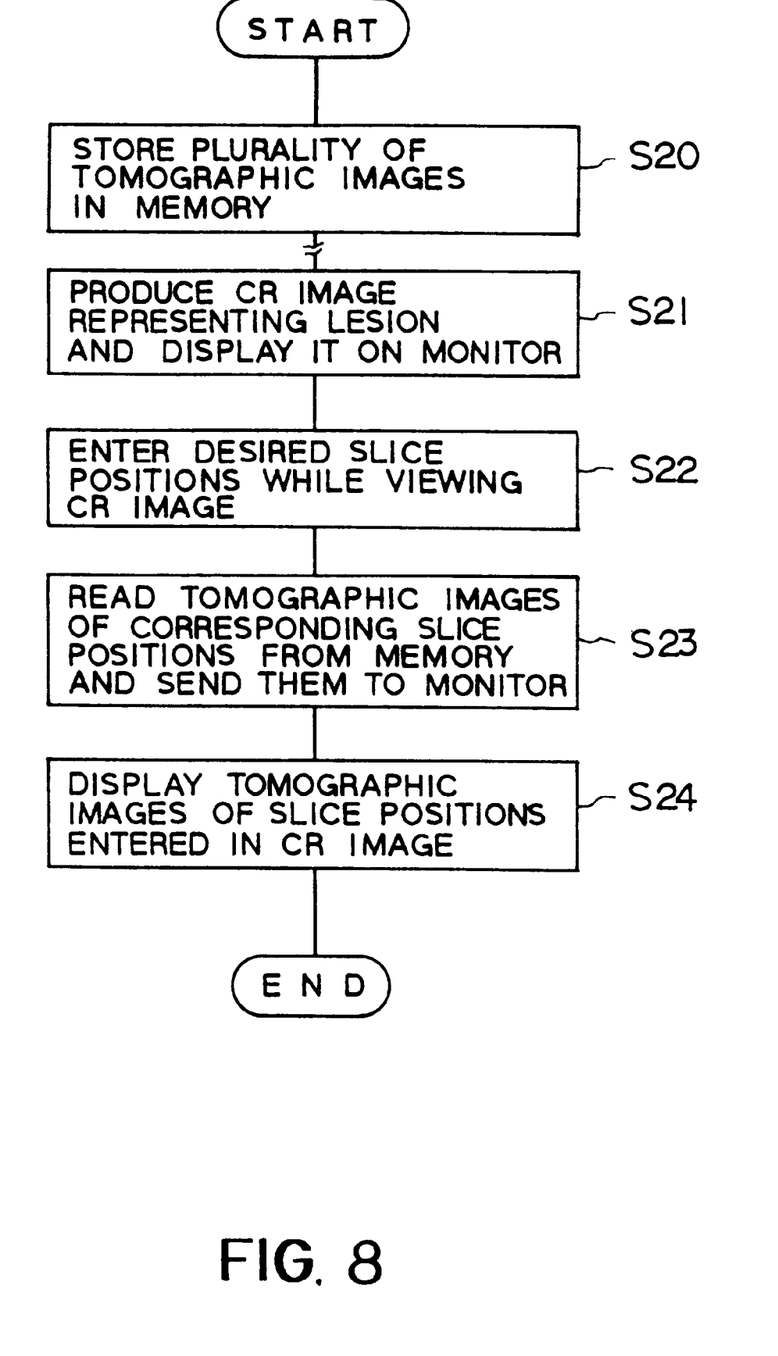
FIG. 8 is a brief flowchart describing an example of processing performed by the whole diagnostic X-ray system of a second embodiment of the invention.

A plurality of tomographic images (slice images) of a given area containing a lesion are produced in advance by means of the X-ray CT scanner 3, and then stored in the memory 31 (step S20). This data storage is carried out by using the Z-directional positions of slices as indices having one-to-one correspondence with slice positions. (In a preferred embodiment, those Z-directional positions of slices may be determined on the manner according to the invention.) After this situation has been obtained or obtained, in the same manner as the foregoing embodiment, a CR image representing the lesion is produced by the X-ray fluoroscopy apparatus 2 and displayed on the monitor 6 (step S21).

At this time, a physician manipulates the keyboard or mouse of the input device 7 so as to enter desired slice positions while viewing the CR image displayed on the monitor 6 (step S22). The input data is, as described previously, sent to the CPU 30 via the interactive display unit 32. The CPU 30 references the plurality of tomographic images stored in the memory 31 according to the sent slice position data. If tomographic images of corresponding slice positions (if a tomographic image of a corresponding slice position is unavailable, a tomographic image of the closest slice position) are read and sent to the monitor 6 via the interactive display unit 32 (step S23). As a result, the tomographic images of slice positions entered in the CR image are displayed on the monitor 6 (step S24).

In short, according to this second embodiment, tomographic images of desired slice positions designated using a CR image can be displayed on the monitor readily and automatically. This is effective in retrieving images stored and displaying them. For example, it is considered that the foregoing processing of step S20 had been carried out for two sets of tomographic CT images acquired before and after placing anti-cancer medicine into a patient body, carrying out processing steps S21 to S24 enables read-out of two frames of tomographic CT images acquired at the same slice position before and after placing anti-cancer medicine and then representation of those two images on the monitor in a divided or any comparative display mode. This makes it easier to compare and study effectiveness of the anti-cancer medicine.

One of systems that have been proposed in the past is a system (IVR-CT angiography system) made by combining an X-ray CT scanner, which is designed to achieve treatment in the course of CT referred to as interventional radiology (IVR) CT, with an X-ray TV system for cardiovascular examination (hereinafter, an angiography system). In this system, insertion of a catheter, which is used to, for example, inject a contrast medium for angiography, into a vessel is achieved with reference made to X-ray TV fluoroscopic images produced by the angiography system and tomographic images produced by the X-ray CT scanner.

However, in the above system, the angiography system and X-ray CT scanner are merely arranged mutually adjacently, and reference is made to fluoroscopic images and tomographic images produced separately. The angiography system and X-ray CT scanner will not mutually communicate slice position information or the like. It takes therefore considerable time to determine slice positions to be scanned by the X-ray CT scanner (of which tomographic images are requested to be produced).

The present invention can be adapted to this kind of system made by combining an X-ray TV fluoroscopy system and an X-ray CT scanner system without exception, and can therefore be adapted to the foregoing IVR-CT angiography system. Specifically, slice position information concerning slice positions suitable for grasping the positional relationship between a vessel and catheter which run together tortously is entered while a CR image produced by the X-ray fluoroscopy apparatus is being viewed. Slice positions to be scanned by IVR CR are automatically set on the basis of the slice position information, and tomographic images of the slice positions are then produced. The time required to determine slice positions to be scanned by an X-ray CT scanner, which is needed in a known IVR-CT angiography system, can therefore be reduced drastically.

In this embodiment, an X-ray fluoroscopy apparatus having an imaging unit that is an I.I.-TV system is used as an apparatus for producing a CR image. The present invention is not limited to the X-ray fluoroscopy apparatus. As long as a digitized fluoroscopic image can be produced, any other X-ray fluoroscopy apparatus, for example, an X-ray fluoroscopy unit using an imaging plate will do.

Furthermore, in the system of this embodiment, tomographic images are displayed on the monitor on which a CR image is displayed. Alternatively, the tomographic images may be displayed on another monitor. Otherwise, the screen of a single monitor may be segmented in order to display an CR image and tomographic images simultaneously. This kind of control is given by the interactive display unit.

There is provided another embodiment in which the processes of step S4 and S5 in FIG. 5 may be changed in processing order with each other. In other words, the slicing start and end positions L1 and L2 may first be corrected on the basis of FIG. 7 and then converted into the distance data n and m.

Further, another embodiment is possible in conjunction with an X-ray CT scanner of the invention. In each embodiment described above, an X-ray fluoroscopy apparatus and an X-ray CT scanner have been described on the assumption that they are provided in a one previously-assembled integration system (i.e. diagnostic X-ray system). However, the X-ray fluoroscopy apparatus and X-ray CT scanner are sometimes manufactured as separate units and combined or integrated at a site. The X-ray scanner of the invention is preferably applied to such a case. Additionally, in such a case, components (e.g. couch portion, console, monitor and input device) used in common by both the apparatus and the scanner may be associated with either of them in the manufacture stage.

The present invention is not limited to the foregoing embodiments and variations. The expert will appreciate that it is possible to combine the various construction details or to supplement or modify them by measures known from the prior art without departing from the scope of the invention.

What is claimed is:

1. An X-ray diagnostic system comprising:
    a couch on which an object to be imaged can be laid and which is used in common for both X-ray fluoroscopy and X-ray computed topography (CT);
    an X-ray fluoroscopy apparatus providing an X-ray fluoroscopic image of the object produced from X-rays transmitted through the object, the X-ray fluoroscopic image being formed pixel by pixel by digital data;
    an X-ray CT scanner, integrated with the X-ray fluoroscopy apparatus, providing a tomographic image of the object;
    means for obtaining, using the X-ray fluoroscopic image, scan plan information including a slice position, said scan plan information being required for the X-ray CT performed by the X-ray CT scanner, the slice position being determined as an actual space value relative to the object; and
    means for providing the X-ray CT scanner the scan plan information;
    wherein the obtaining means comprises,
        means for enabling an operator manually to specify a desired position on the X-ray fluoroscopic image,
        first means for calculating first positional information representing an absolute position of the X-ray fluoroscopic image located in an actual space formed by the object,
        second means for calculating second positional information given by the pixel corresponding to the specified desired position in the X-ray fluoroscopic image, and
        third means for calculating the slice position based on both the first and second positional information.

2. The X-ray diagnostic system of claim 1, further comprising:
    a storage member storing data of the tomographic image formed by a plurality of frames acquired by the X-ray CT scanner and slice position indexing information by which the plurality of frames acquired by the X-ray CT scanner are indexed frame by frame with information of a position sliced by the X-ray CT scanner,
    means for retrieving among the plurality of frames of the tomographic image data stored in the storage member data of a tomographic image corresponding to the slice position obtained by the obtaining means, and
    means for displaying the retrieved tomographic image data.

3. The X-ray diagnostic system of claim 1, wherein said X-ray fluoroscopy apparatus comprises:
    an X-ray source radiating the X-rays,
    an imaging unit detecting the transmitted X-rays,
    a converter converting outputs of the imaging unit into the digital image data, and
    a monitor visualizing the digital image data as the X-ray fluoroscopic image.

4. The X-ray diagnostic system of claim 3, wherein said X-ray fluoroscopy apparatus comprises a supporting arm member supporting at both ends thereof both the X-ray source and the imaging unit face to face a predetermined distance apart from each other.

5. The X-ray diagnostic system of claim 1, wherein said first calculating means calculates, as the first positional information, actual-space distance information between a reference position preset on the object and the X-ray fluoroscopic image of the object.

6. The X-ray diagnostic system of claim 5, wherein said second calculating means calculates, as the second positional information, a size of each pixel of the X-ray fluoroscopic image and the number of pixels forming the specified desired position in the X-ray fluoroscopic image.

7. The X-ray diagnostic system of claim 1, wherein said X-ray CT scanner comprises a gantry having a set rotation center about which the X-ray CT is performed,
    the system further comprising:
        means for correcting information indicative of the slice position into information indicative of another slice position being in accord with a height of the rotation center.

8. The X-ray diagnostic system of claim 1, wherein said X-ray fluoroscopy apparatus is formed by an X-ray TV system for cardiovascular examination constituting an interventional radiology (IVR)-CT/angiography system, together with the X-ray CT scanner.

9. In an X-ray diagnostic system comprising an X-ray fluoroscopy apparatus and an X-ray CT scanner, both of which are integrated to each other, and a couch on which an object to be imaged can be lain which can be used in common by the X-ray fluoroscopy apparatus and the X-ray CT scanner, a method of positioning the X-ray CT scanner, comprising the steps of:
    using the X-ray fluoroscopy apparatus, producing an X-ray fluoroscopic image of the object produced from X-rays transmitted through the object subjected to fluoroscopic X-rays, the X-ray fluoroscopic image being formed pixel by pixel by digital data;
    manually specifying a desired position on the X-ray fluoroscopic image;
    first calculating first positional information representing an absolute position of the X-ray fluoroscopic image located in an actual space formed by the object;
    second calculating second positional information given by a pixel corresponding to the manually specified desired position in the X-ray fluoroscopic image;
    third calculating a slice position based on both the first and second positional information, the slice position being determined as an actual space value concerning the object; and
    providing information about the slice position as part of scan plan information to the X-ray CT scanner.

* * * * *